US005874288A

United States Patent [19]
Thompson et al.

[11] Patent Number: 5,874,288

[45] Date of Patent: Feb. 23, 1999

[54] ***BACILLUS THURINGIENSIS* TOXINS WITH IMPROVED ACTIVITY**

[75] Inventors: Mark Thompson, San Diego; Mark Knuth; Guy Cardineau, both of Poway, all of Calif.

[73] Assignee: Mycogen Corporation, San Diego, Calif.

[21] Appl. No.: 904,278

[22] Filed: Jul. 31, 1997

[51] Int. Cl.[6] .............................. C12N 15/32; C12N 1/21; C12N 15/63; C12N 5/10

[52] U.S. Cl. .................. 435/252.3; 536/23.1; 536/23.71; 435/419; 435/252.33; 435/252.34; 435/320.1; 424/93.2; 800/302

[58] Field of Search ............................... 536/23.1, 23.71; 435/419, 252.3, 320.1, 252.33, 252.34; 424/93.2; 800/302

[56] References Cited

U.S. PATENT DOCUMENTS

| | | | |
|---|---|---|---|
| 4,448,885 | 5/1984 | Schnepf et al. | 435/253 |
| 4,467,036 | 8/1984 | Schnepf et al. | 435/317 |
| 4,797,276 | 1/1989 | Herrnstadt et al. | 424/84 |
| 4,849,217 | 7/1989 | Soares et al. | 24/93 |
| 4,853,331 | 8/1989 | Herrnstadt et al. | 435/252.1 |
| 4,918,006 | 4/1990 | Ellar et al. | 435/69.1 |
| 4,948,734 | 8/1990 | Edwards et al. | 435/252.5 |
| 4,990,332 | 2/1991 | Payne et al. | 424/93 |
| 5,039,523 | 8/1991 | Payne et al. | 424/93 |
| 5,093,120 | 3/1992 | Edwards et al. | 424/93 |
| 5,126,133 | 6/1992 | Payne et al. | 424/93 |
| 5,151,363 | 9/1992 | Payne | 435/252.5 |
| 5,164,180 | 11/1992 | Payne et al. | 424/93 L |
| 5,169,629 | 12/1992 | Payne et al. | 424/93 L |
| 5,186,934 | 2/1993 | Narva et al. | 424/93 A |
| 5,208,017 | 5/1993 | Bradfisch et al. | 424/84 |
| 5,236,843 | 8/1993 | Narva et al. | 435/252.3 |
| 5,247,786 | 9/1993 | Payne et al. | 424/93.461 |
| 5,262,159 | 11/1993 | Payne et al. | 424/93 L |
| 5,262,399 | 11/1993 | Hickle et al. | 514/12 |
| 5,270,448 | 12/1993 | Payne | 530/350 |
| 5,281,530 | 1/1994 | Sick et al. | 435/252.3 |
| 5,286,485 | 2/1994 | Uyeda et al. | 424/93 L |
| 5,322,932 | 6/1994 | Narva et al. | 530/350 |
| 5,350,577 | 9/1994 | Payne | 424/93.461 |
| 5,426,049 | 6/1995 | Sick et al. | 435/252.3 |
| 5,439,881 | 8/1995 | Narva et al. | 514/2 |
| 5,468,636 | 11/1995 | Payne et al. | 435/252.3 |

FOREIGN PATENT DOCUMENTS

| | | |
|---|---|---|
| 0462721 | 6/1991 | European Pat. Off. . |
| 9219739 | 11/1992 | WIPO . |

OTHER PUBLICATIONS

Prichard, R.K., et al. (1980) "The Problem of Anthelmintic Resistance in Nematodes" Australian Veterinary Journal. vol. 56, pp. 239–251.

Coles, G.C. (1986) "Anthelmintic Resistance in Sheep" Veterinary Clinics of North America, Food Animal Practice. 2:2(423–432).

Ignoffo, C.M. et al., "Deleterious Effects of the Thermostable Toxin of *Bacillus thuringiensis* on Species of Soil–Inhabiting, Myccliophagus, and Plant–Parasitic Nematodes" Journal of the Kansas Entomological Society. 50:3(394–398).

Bottjer, Kurt P., et al. (1985) "Nematoda: Susceptability of the Egg to *Bacillus thuringiensis* Toxins" Experimental Parasitology. 60:239–244.

Gaertner, F. and Leo Kim, (1988) "Current Applied Recombinant DNA Projects" TIBTECH. 6:4(54–57).

Couch, T.L. (1980) "Mosquito Pathogenicity of *Bacillus thuringiensis* var. *israelensis*" in Developments in Industrial Microbiology. 22:61–76.

Beegle, C.C. (1978) "Use of Entomogenous Bacteria in Agroccosystems" Developments in Industrial Microbiology. 20:97–104.

Krieg, V.A., et al. (1983) "*Bacillus thuringiensis* var. *tenebrionis*: a new pathotype effective against larvae of Coleoptera." Z. Ang. Ent. 96:500–508.

Hofte, H., H.R. Whiteley (1989) "Insecticidal Crystal Proteins of *Bacillus thuringiensis*" Microbiological Reviews. 53:2(242–255).

Feitelson, J.S., et al. (1992) "*Bacillus thuringiensis*: Insects and Beyond" Bio/Technology. 10:271–275.

Schnepf, H.E., and H.R. Whiteley (1981) "Cloning and Expression of the *Bacillus thuringiensis* Crystal Protein Gene in *Escheria coli*" Proc. Natl. Acad. Sci. USA. 78:5(2893–2897).

Ciordia and W.E. Bizzel (1961) "A Preliminary Report on the Effects of *Bacillus thuringiensis* var. *thuringiensis* Berliner on the Development of the Free–Living Stages of Some Cattle Nematodes" Jour. of Parasitology 47:41 (Abstract).

Gaertner, F.H. (1989) "Cellular Delivery Systems for Insecticidal Proteins: Living and Non–Living Microorganisms" in *Controlled Delivery of Crop–Protection Agents,* R.M. Wilkins, ed., Taylor and Francis, New York and London, 1990, pp. 245–255.

Schnepf, H.E., et al. (1985) "The Amino Acid Sequence of a Crystal Protein from *Bacillus thuringiensis* Deduced from the DNA Base Sequence" The Journal of Biological Chemistry. 260:10(6264–6272).

Crickmore, N., et al. (1996) Society for Invertebrate Pathology at the 29th Annual Meeting, the 3rd International Colloquium on *Bacillus thuringiensis* and the University of Cordoba. Sep. 1–6, 1996. Abstract.

Wabiko, H., et al. (1986) "*Bacillus thuringiensis* Entomocidal Protoxin Gene Sequence and Gene Product Analysis." DNA. 5:4(305–314).

Adang, M.J., et al. (1985) "Characterized Full–Length and Truncated Plasmid Clones of the Crystal Protein of *Bacillus thuringiensis* subsp. *kurstaki* HD–73 and Their Toxicity to *Manduca sexta*" Gene 36:289–300.

(List continued on next page.)

*Primary Examiner*—Rebecca E. Prouty
*Attorney, Agent, or Firm*—Saliwanchik, Lloyd & Saliwanchik

[57] ABSTRACT

The subject invention pertains to B.t. toxins active against pests. More specifically, the subject invention pertains to truncated Cry6A toxins. These activated toxins are particularly effective for controlling coleopteran pests such as the corn rootworm and the alfalfa weevil.

8 Claims, 1 Drawing Sheet

OTHER PUBLICATIONS

Nicholls, C.N., et al. (1989) "Evidence for Two Different Types of Insecticidal P2 Toxins with Dual Specificity in *Bacillus thuringiensis* Subspecies" Journal of Bacteriology, 171(9):5141–5147.

M.A. Pfannensteil et al., "Toxicity of Protease–Resistant Domains From the Delta–Endotoxin of *Bacillus thuringiensis* subsp. *israelensis* in *Culex quinquefasciatus* and *Aedes aegypti* Bioassays", Appl. Environ. microbiol. 56(1): 162–166, Jan. 1990.

U. Nagamatsu et al., "A Toxic Fragment From the Entomodicidal Crystal Protein of *Bacillus thuringiensis*", Agric. Biol. Chem. 48(3): 611–619, Mar. 1984.

J.N. Aronson et al., "Toxic Trypsin Digest Fragment From the *Bacillus thuringiensis* Parasporal Protein", Appl. Environ. Microbiol. 53(2): 416–421, Feb. 1987.

D. Bosch et al., "Recombinant *Bacillus thuringiensis* Crystal Proteins With New Properties: Possibilities for Resistance Management", Bio/Technology 12(9): 915–918, Sep. 1994.

G. Honee et al., A Translation Fusion Product of Two Different Insecticidal Crystal Protein Genes of *Bacillus thuringiensis* Exhibits an Enlarged Insecticidal Spectrum, Appl. Environ. Microbiol. 56(3): 823–825, Mar. 1990.

H. E. Schnepf et al., Delineation of a Toxin–Encoding Segment of a *Bacillus thuringiensis* Crystal Protein Gene, 260(10): 6273–6280, May 1985.

Figure 1
Lineup of 86A1 (top line) with 69D1 (bottom line)

```
  1 MIIDSKTTLPRH...SLIHTIKLNSNKK...YGPGDMTNGNQFIISKQEW 44
    ||::. .|||:|   . | ... .|.||   .||::|.. :.|||||:||
  1 MILGNGKTLPKHIRLAHIFATQNSSAKKDNPLGPEGMVTKDGFIISKEEW 50
             .         .         .         .         .
 45 ATIGAYIQTGLGLPVNEQQLRTHVNLSQDISIPSDFSQLYDVYCSDKTSA 94
    | :.||: || |||:|::::| ||.|.  | ||.||.|||.|| .||  .
 51 AFVQAYVTTGTGLPINDDEMRRHVGLPSRIQIPDDFNQLYKVYNEDKHLC 100
             .         .         .         .         .
 95 EWWNKNLYPLIIKSANDIASYGFKVAGDPSIKKDGYFKKLQDELDNIVDN 144
    .|||  |:||::|.||||..||||.||....|  ||:. :||:::|| ||
101 SWWNGFLFPLVLKTANDISAYGFKCAGKGATK..GYYEVMQDDVENISDN 148
             .         .         .         .         .
145 NSDDDAIAKAIKDFKARCGILIKEAKQYEEAAKNIVTSLDQFLHGDQ... 191
    . |. | .|| ||:.||| ||||||.||..||.:: . |: ||.|:|
149 GYDKVAQEKAHKDLQARCKILIKEADQYKAAADDVSKHLNTFLKGGQDSD 198
             .         .         .         .         .
192 .KKLEGVINIQKRLKEVQTALNQAHGESSPAHKELLEKVKNLKTTLERTI 240
     ..: || .:| .| :|...|:. .|:.|| |.|||.||.:||..|| .|
199 GNDVIGVEAVQVQLAQVKDNLDGLYGDKSPRHEELLKKVDDLKKELEAAI 248
             .         .         .         .         .
241 KAEQDLEKKVEYSFLLGPLLGFVVYEILENTAVQHIKNQIDEIKKQLDSA 290
    |||.:|||||. || |||||||||||||| |||. |...::.:. :||.|
249 KAENELEKKVKMSFALGPLLGFVVYEILELTAVKSIHKKVEALQAELDTA 298
             .         .         .         .         .
291 QHDLDRDVKIIGMLNSINTDIDNLYSQGQEAIKVFQKLQGIWATIGAQIE 340
    ..:|||||||:||:|||:|||||:..||::|: ||.|:.|||..|: .|:
299 NDELDRDVKILGMMNSIDTDIDNMLEQGEQALVVFRKIAGIWSVISLNIG 348
             .         .         .         .         .
341 NLRTTSLQEVQDSDDADEIQIELEDASDAWLVVAQEARDFTLNAYSTNSR 390
    |||.|||.|::::.:|.|.: |||:||.:.|  :|:||..|.||||..
349 NLRETSLKEIEEENDDDALYIELGDAAGQWKEIAEEAQSFVLNAYTP... 395
             .         .         .         .         .
391 QNLPINVISDSCNCSTTNMTSNQYSNPTTNMTSNQYMISHEYTSLPNNFM 440
    .         .         .         .


441 LSRNSNLEYKCPENNFMIYWYNNSDWYNNSDWYNN                475
```

*BACILLUS THURINGIENSIS* TOXINS WITH IMPROVED ACTIVITY

BACKGROUND OF THE INVENTION

Insects and other pests cost farmers billions of dollars annually in crop losses and in the expense of keeping these pests under control. The losses caused by pests in agricultural production environments include decrease in crop yield, reduced crop quality, and increased harvesting costs.

Coleopterans are an important group of agricultural pests which cause a very large amount of damage each year. Examples of coleopteran pests include alfalfa weevils and corn rootworm.

The alfalfa weevil, *Hypera postica,* and the closely related Egyptian alfalfa weevil, *Hypera brunneipennis,* are the most important insect pests of alfalfa grown in the United States, with 2.9 million acres infested in 1984. An annual sum of 20 million dollars is spent to control these pests. The Egyptian alfalfa weevil is the predominant species in the southwestern U.S., where it undergoes aestivation (i.e., hibernation) during the hot summer months. In all other respects, it is identical to the alfalfa weevil, which predominates throughout the rest of the U.S.

The larval stage is the most damaging in the weevil life cycle. By feeding at the alfalfa plant's growing tips, the larvae cause skeletonization of leaves, stunting, reduced plant growth, and, ultimately, reductions in yield. Severe infestations can ruin an entire cutting of hay. The adults, also foliar feeders, cause additional, but less significant, damage.

Approximately 9.3 million acres of U.S. corn are infested with corn rootworm species complex each year. The corn rootworm species complex includes the northern corn rootworm, *Diabrotica barberi,* the southern corn rootworm, *D. undecimpunctata howardi,* and the western corn rootworm, *D. virgifera virgifera.* The soil-dwelling larvae of these *Diabrotica* species feed on the root of the corn plant, causing lodging. Lodging eventually reduces corn yield and often results in death of the plant. By feeding on cornsilks, the adult beetles reduce pollination and, therefore, detrimentally effect the yield of corn per plant. In addition, members of the genus *Diabrotica* attack cucurbit crops (cucumbers, melons, squash, etc.) and many vegetable and field crops in commercial production as well as those being grown in home gardens.

Control of corn rootworm has been partially addressed by cultivation methods, such as crop rotation and the application of high phosphate levels to stimulate the growth of an adventitious root system. In addition, an emerging two-year diapause (or overwintering)trait of Northern corn rootworms is disrupting crop rotation in some areas. However, chemical insecticides are relied upon most heavily to guarantee the desired level of control. Insecticides are either banded onto or incorporated into the soil. The major problem associated with the use of chemical insecticides is the development of resistance among the treated insect populations.

Over $250 million worth of insecticides are applied annually to control corn rootworms alone in the United States. Even with insecticideuse, rootworms cause over $750 million worth of crop damage each year, making them the most serious corn insect pest in the Midwest.

Damage to plants caused by nematodes is also a prevalent and serious economic problem. Nematodes cause widespread and serious damage in many plant species. Many genera of nematodes are known to cause such damage. Plant-parasitic nematodes include members of the Phylum Nematoda, Orders Tylenchida and Dorylaimide. In the Order Tylenchida, the plant-parasitic nematodes are found in two Super Families: Tylenchoidea and Criconematoidea. There are more than 100,000 described species of nematodes.

Chemical pesticides have provided an effective method of pest control; however, the public has become concerned about the amount of residual chemicals that might be found in food, ground water, and the environment. Stringent new restrictions on the use of pesticides and the elimination of some effective pesticides form the marketplace could limit economical and effective options for controlling costly pests. Thus, there is an urgent need to identify pest control methods and compositions which are not harmful to the environment.

Nematicides routinely used for control of plant-parasitic nematodes are rapidly being pulled from the market as concern for environmental safety increases. In the year 2001, Methyl Bromide, a mainstay in the control of such parasites, will no longer be marketed in the United States. Therefore, less harmful control agents are clearly needed.

The use of chemical pesticides to control corn rootworm and other coleopteran pests, as well as nematodes, has several drawbacks. Pesticide use often raises environmental concerns such as contamination of soil and of both surface and underground water supplies. Working with pesticides may also pose hazards to the persons applying them.

The regular use of chemical pesticides for the control of unwanted organisms can select for chemical resistant strains. Chemical resistance occurs in many species of economically important insects and has also occurred in nematodes of sheep, goats, and horses. The regular use of chemical toxins to control unwanted organisms can select for drug-resistant strains. This has occurred in many species of economically important insects and has also occurred in nematodes of sheep, goats, and horses. For example, an accepted methodology for control of nematodes has centered around the drug bennimidazole and its congeners. The use of these drugs on a wide scale has led to many instances of resistance among nematode populations (Prichard, R. K. et al. [1980] "The problem of anthelmintic resistance in nematodes," Austr. Vet. J 56:239–251; Coles, G. C. [1986] "Anthelmintic resistance in sheep," In Veterinary Clinics of North America: Food Animal Practice, Vol 2:423–432 [Herd, R. P., eds.] W. B. Saunders, New York). There are more than 100,000 described species of nematodes. The development of pesticide resistance necessitates a continuing search for new control agents having different modes of action.

At the present time there is a need to have more effective means to control the many coleopterans and nematodes that cause considerable damage to susceptible hosts and crops. Advantageously, such effective means would employ specific biological agents.

The soil microbe *Bacillus thuringiensis* (B.t.) is a Gram-positive, spore-forming bacterium characterized by parasporal crystalline protein inclusions. These inclusions often appear microscopically as distinctively shaped crystals. The proteins can be highly toxic to pests and specific in their toxic activity. Certain B.t. toxin genes have been isolated and sequenced, and recombinant DNA-based B.t. products have been produced and approved for use. In addition, with the use of genetic engineering techniques, new approaches for delivering these B.t. endotoxins to agricultural environments are under development, including the use of plants genetically engineered with endotoxin genes for insect resistance and the use of stabilized intact microbial cells as B.t. endotoxin delivery vehicles (Gaertner, F. H., L. Kim [1988] TIBTECH6:S4–S7). Thus, isolated B.t. endotoxin genes are becoming commercially valuable.

Until fairly recently, commercial use of B.t. pesticides has been largely restricted to a narrow range of lepidopteran (caterpillar) pests. Preparations of the spores and crystals of *B. thuringiensis* subsp. *kurstaki* have been used for many years as commercial insecticides for lepidopteran pests. For example, *B. thuringiensis* var. *kurstaki* HD-1 produces a crystalline δ-endotoxin which is toxic to the larvae of a number of lepidopteran insects.

In recent years, however, investigators have discovered B.t. pesticides with specificities for a much broader range of pests. For example, other species of B.t., namely israelensis and morrisoni (a.k.a. tenebrionis, a.k.a. B.t. M-7, a.k.a. B.t. san diego), have been used commercially to control insects of the orders Diptera and Coleoptera, respectively (Gaertner, F. H. [1989] "Cellular Delivery Systems for Insecticidal Proteins: Living and Non-Living Microorganisms," in Controlled Delivery of Crop Protection Agents, R. M. Wilkins, ed., Taylor and Francis, New York and London, 1990, pp. 245–255.). See also Couch, T. L. (1980) "Mosquito Pathogenicity of Bacillus thuringiensis var. israelensis," Developments in Industrial Microbiology 22:61–76; and Beegle, C. C., (1978) "Use of Entomogenous Bacteria in Agroecosystems," Developments in Industrial Microbiology 20:97–104. Krieg, A., A. M. Huger, G. A. Langenbruch, W. Schnetter (1983) Z. ang. Ent. 96:500–508, describe Bacillus thuringiensis var. tenebrionis, which is reportedly active against two beetles in the order Coleoptera. These are the Colorado potato beetle, *Leptinotarsa decemlineata,* and *Agelastica alni.*

More recently, new subspecies of B.t. have been identified, and genes responsible for active δ-endotoxin proteins have been isolated (Höfte, H., H. R. Whiteley [1989] Microbiological Reviews 52(2):242–255). Höfte and Whiteley classified B.t. crystal protein genes into four major classes. The classes were CryI (Lepidoptera-specific), CryII (Lepidoptera- and Diptera-specific), CryIII (Coleoptera-specific), and CryIV (Diptera-specific). The discovery of strains specifically toxic to other pests has been reported (Feitelson,J. S., J. Payne, L. Kim [1992] Bio/Technology 10:271–275). CryV was proposed to designate a class of toxin genes that are nematode-specific. Other classes of B.t. genes have now been identified.

The 1989 nomenclature and classification scheme of H öfte and Whiteley for crystal proteins was based on both the deduced amino acid sequence and the host range of the toxin. That system was adapted to cover 14 different types of toxin genes which were divided into five major classes. As more toxin genes were discovered, that system started to become unworkable, as genes with similar sequences were found to have significantly different insecticidal specificities. The number of sequenced *Bacillus thuringiensis* crystal protein genes currently stands at about 50. A revised nomenclature scheme has beenproposed which is based solely on amino acid identity (Crickmore et al. [1996] Society for Invertebrate Pathology, 29th Annual Meeting, IIIrd International Colloquium on Bacillus thuringiensis, University of Cordoba, Cordoba, Spain, September 1–6, abstract). The mnemonic "cry" has been retained for all of the toxin genes except cyta and cytB, which remain a separate class. Roman numerals have been exchanged for Arabic numerals in the primary rank, and the parentheses in the tertiary rank have been removed. Many of the original names have been retained, with the noted exceptions, although a number have been reclassified.

The cloning and expression of a B.t. crystal protein gene in *Escherichia coli* has been described in the published literature (Schnepf, H. E., H. R. Whiteley (1981) Proc. Natl. Acad. Sci. USA 78:2893–2897). U.S. Pat. No. 4,448,885 and U.S. Pat. No. 4,467,036 both disclose the expression of B.t. crystal protein in *E. coli.* U.S. Pat. Nos. 4,990,332; 5,039,523; 5,126,133; 5,164,180; 5,169,629; and 5,286,485 are among those which disclose B.t. toxins having activity against lepidopterans. U.S. Pat. Nos. 4,797,276 and 4,853,331 disclose *B. thuringiensis* strain tenebrionis which can be used to control coleopteran pests in various environments. U.S. Pat. No. 4,918,006 discloses B.t. toxins having activity against dipterans.

A small number of research articles have been published about the effects of delta endotoxins from *B. thuringiensis* species on the viability of nematode eggs. Bottjer, Bone and Gill, ([1985] Experimental Parasitology 60:239–244)have reported that B.t. kurstaki and B.t. israelensis were toxic in vitro to eggs of the nematode *Trichostrongylus colubriformis.* In addition, 28 other B.t. strains were tested with widely variable toxicities. Ignoffo and Dropkin ([1977] J Kans. Entomol. Soc. 50:394–398) have reported that the thermostable toxin from *Bacillus thuringiensis* (beta exotoxin) was active against a free-living nematode, *Panagrellus redivivus* (Goodey); a plant-parasitic nematode, *Meloidogyne incognita* (Chitwood); and a fungus-feeding nematode, *Aphelenchus avena* (Bastien). Beta exotoxin is a generalized cytotoxic agent with little or no specificity. Also, Ciordia and Bizzell ([1961] Jour. of Parasitology 47:41 [abstract]) gave a preliminary report on the effects of *B. thuringiensis* on some cattle nematodes.

U.S. Pat. No. 5,151,363 and U.S. Pat. No. 4,948,734 disclose certain isolates of B.t. which have activity against nematodes. Other U.S. Patents which disclose activity against nematodes include 5,093,120; 5,236,843; 5,262,399; 5,270,448; 5,281,530; 5,322,932; 5,350,577; 5,426,049; and 5,439,881. As a result of extensive research and investment of resources, other patents have issued for new B.t. isolates and new uses of B.t. isolates. See Feitelson et al, supra, for a review. However, the discovery of new B.t. isolates and new uses of known B.t. isolates remains an empirical, unpredictable art.

Some *Bacillus thuringiensis* toxins which are active against corn rootworm and other coleopterans are now known. For example, U.S. Pat. No. 4,849,217 discloses various isolates, including PS52A1 and PS86A1, as having activity against alfalfa weevils. U.S. Pat. No. 5,208,017 discloses PS86A1 as a having activity against Western corn rootworm. U.S. Pat. Nos.5,427,786and 5,186,934each disclose B.t. Isolates and toxins active against coleopterans. Specifically disclosed in these patents is the isolate known as PS86A1 and a coleopteran-active toxin obtainable therefrom known as 86A1. Toxin 86A1 is now also known as Cry6A (CryVIA). The wild-type Cry6A toxin is about 54–58 kDa.

A Cry6B toxin is also known. This toxin can be obtained from the PS69D1 isolate. The full length Cry6A and Cry6B toxins are known to have activity against nematodes. The following U.S. Patents disclose, in part, the PS69D1 isolate as having activity against nematodes: 4,948,734; 5,093,120; 5,262,399; and 5,439,881.

A generic formula for the amino acid sequence of CryVI toxins has been disclosed in WO 92/19739, which also teaches that the full length toxin has activity against nematodes. The PS52A1 and PS69D1 isolates are disclosed therein. U.S. Pat. Nos. 5,262,159 and 5,468,636 also disclose a generic formula for toxins having activity against aphids.

Although the Cry6A toxin was known to inhibit the growth of certain coleopterans, it was not previously known that this toxin could be activated by truncation to yield a toxin that is lethal to coleopterans, such as the western corn rootworm. In addition, there was no suggestion that the truncated Cry6A would be active against nematodes.

Some previous examples of truncations to other B.t. toxins are known in the art. For example, the P2 (Cry2) toxins (Nicholles, E. N., W. Ahmad, D. J. Ellar [1989] J Bact. 171:5141–5147) exist as 61–63 kDa proteins. Proteolysistrims about 5 kDa off, leaving 56–58 kDa proteins. However, toxicity either remained unchanged or was worse by a factor of 10. Furthermore, these proteins share no significant homology with Cry6 toxins. Other articles which address certain aspects of the activity and/or function of portions of B.t. toxins include Adang, M. J., M. J. Staver, T. A. Rocheleau et al. (1985) Gene 36:289–300; Wabiko, H., K. C. Raymond, L. A. Bulla, Jr. (1986) DNA 5:305–314 (Medline 863000920); Schnepf, H. E, H. R. Whiteley (1985) J Biol. Chem. 260:6273–6280; U.S. Pat. No. 5,468,636; U.S. Pat. No. 5,236,843; and EP 0462721.

The use of truncation to obtain activated Cry6A toxins as described below is completely new to the B.t. art.

BRIEF SUMMARY OF THE INVENTION

The subject invention concerns materials and methods useful in the control of pests and, particularly, plant pests. Specifically, the subject invention provides new truncated B.t. toxins useful for the control of coleopteran pests, including corn rootworm. The subject invention further provides toxins useful for the control of nematodes. The subject invention farther provides nucleotide sequences which encode these toxins.

In a preferred embodiment of the subject invention, truncated forms of cry6A B.t. toxins have been found to be particularly active against corn rootworm. Truncated toxins described herein can also be used to control nematodes. Specifically exemplified herein is a truncated cry6A toxin which has amino acids removed from the N-terminus and the C-terminus and is about 40–50 kDa. In a preferred embodiment, the toxins of the subject invention are produced by genes which encode the highly active truncated proteins. As described herein, the truncated toxins of the subject invention can also be obtained through treatment of B.t. culture supernatants and/or by growing B.t. cultures under appropriate conditions to result in the production of active toxins as a result of the advantageous effects of proteases. Similarly, protein expressed by a recombinant host may be treated to obtain the truncated toxin.

In a preferred embodiment, the genes described herein which encode pesticidal toxins are used to transform plants in order to confer pest resistance upon said plants. Such transformation of plants can be accomplished using techniques well known to those skilled in the art and would typically involve modification of the gene to optimize expression of the truncated toxin in plants.

The subject invention also concerns the use of all or part of the truncated toxins and genes in the production of fusion proteins and fusion genes.

BRIEF DESCRIPTION OF THE DRAWING

FIG. 1 is an amino acid by amino acid comparison of 86A1 and 69D1.

BRIEF DESCRIPTION OF THE SEQUENCES

SEQ ID NO. 1 is the nucleotide sequence of a full-length cry6A gene.

SEQ ID NO. 2 is the amino acid sequence of a full-length Cry6A toxin.

SEQ ID NO. 3 is a full-length plant-optimized gene sequence for cry6A/86A1 gene.

SEQ ID NO. 4 is the fill-length amino acid sequence encoded by SEQ ID NO. 3.

SEQ ID NO. 5 is the R443 truncated gene sequence.

SEQ ID NO. 6 is the amino acid sequence encoded by SEQ ID NO. 5.

SEQ ID NO. 7 is the truncated plant-optimized R390 gene sequence.

SEQ ID NO. 8 is the truncated protein sequence encoded by SEQ ID NO. 7.

SEQ ID NO. 9 is the nucleotide sequence of a fill length cry6B/69D1 gene.

SEQ ID NO. 10 is the amino acid sequence of a full length Cry6B/69D1 toxin.

DETAILED DISCLOSURE OF THE INVENTION

The subject invention concerns materials and methods for the control of pests. In specific embodiments, the subject invention pertains to truncated B.t. toxins having activity against coleopteran pests. The subject invention also provides toxins useful in the control of nematodes. The subject invention further concerns novel genes which encode these pesticidal toxins. In a particularly preferred embodiment, the materials and methods described herein can be used to control corn rootworm.

Isolates useful according to the subject invention are available to those skilled in the art by virtue of deposits described in various U.S. Patents, including U.S. Pat. No. 5,427,786; 5,186,934; and 5,273,746. See also PCT international application number WO 93/04587. The PS86A1 (NRRL B-1 8400, deposited Aug. 16, 1988) and MR506 microbes are disclosed in these patents. The PS69D1 isolate (NRRL B-18247, deposited Jul. 28, 1987) has been disclosed in various U.S. Pat. Nos. including: 4,948,734; 5,093,120; 5,262,399; and 5,439,881.

The B.t. PS86A1 isolate produces an approximately 55 kDa toxin is referred to as the 86A1 or 86Al (a) toxin. This toxin is a Cry6A toxin. The gene encoding this toxin has been cloned into Bacillus thuringiensis isolate MR506, which also expresses the Cry6A toxin.

In a preferred embodiment of the subject invention, the approximately 55 kDa Cry6A toxin expressed by B.t. isolates PS86A1 and MR506 is truncated to yield a toxin of approximately 45 kDa having high biological activity against coleopterans. This type of truncated toxin is referred to herein as the truncated Cry6A toxin. Advantageously, this truncated toxin has been found to be particularly active against corn rootworm. This truncated toxin preferably has amino acids removed from the N-terminus and the C-terminus to yield the active truncated forms. However, truncated, activated toxins according to the subject invention may also be obtained by removing amino acids from either the N-terminus, only, or the C-terminus, only.

As described herein, the removal of amino acids to yield the truncated active form can be accomplished using a variety of techniques. In a preferred embodiment, the gene is modified to encode the active truncated form of the toxin. Alternatively, the truncated toxins of the subject invention can be obtained by treatment of B.t. cultures or growing the cultures under appropriate conditions such that endogenous proteases cleave the protein to its highly active form.

The removal of portions of the N-terminus and the C-terminus of the 86A1 55 kDa toxin was found to result in an advantageous activation of this toxin which increased the potency of its activity. Removal of amino acids can be accomplished by treatment with trypsin, preferably, or with another appropriate enzyme, or enzyme mixture, such as Pronase, chymotrypsin, or endogenous proteases in B.t. culture broths. Trypsin concentration, time of incubation, and temperature are interdependent conditions and could be varied by a person skilled in the art to obtain the desired final product of the digestion. Other biologically active fragments can be obtained by those skilled in the art using the teachings provided herein. Fragments having amino and/or carboxyl termini similar to that identified above would also show improved insecticidal activity.

As those skilled in the art having the benefit of this disclosure would readily recognize, the specific media used to grow the B.t. culture can be modified to achieve optimum activation of the B.t. toxin. For example, the cell density can be modulated by adjusting or changing the culture medium. Also, media having proteases therein can be used to enhance the activation of the B.t. toxins.

The full length B.t. toxins of about 55 kDa can be expressed and then converted to highly active forms through addition of appropriate reagents and/or by growing the cultures under conditions which result in the truncation of the proteins through the fortuitous action of endogenous proteases. In an alternative embodiment, the full length toxin may undergo other modifications to yield the active form of the toxin. Adjustment of the solubilization of the toxin, as well as other reaction conditions, such as pH, ionic strength, or redox potential, can be used to effect the desired modification of the full length toxin to yield an active form.

One recombinant host which can be used to obtain the truncated toxin of the subject invention is MR506. The truncated toxin of the subject invention can be obtained by treating the crystalline δ-endotoxin of *Bacillus thuringiensis* strain MR506 with a serine protease such as bovine trypsin at an alkaline pH and preferably in the absence of β-mercaptoethanol.

The subject invention also concerns the use of all or part of the truncated toxins and genes in the production of fusion proteins and fusion genes.

Genes and toxins. The genes and toxins useful according to the subject invention include not only the sequences specifically exemplified but also shorter sequences, and variants, mutants, and fusion proteins which retain the characteristic pesticidal activity of the toxins specifically exemplified herein. As used herein, the terms "variants" or "variations" of genes refer to nucleotide sequences which encode the same toxins or which encode equivalent toxins having pesticidal activity. As used herein, the term "equivalent toxins" refers to toxins having the same or essentially the same biological activity against the target pests as the exemplified toxins.

It should be apparent to a person skilled in this art that genes encoding active toxins can be identified and obtained through several means. The specific genes exemplified herein may be obtained from the isolates deposited at a culture depository as described above. These genes, or portions or variants thereof, may also be constructed synthetically, for example, by use of a gene synthesizer. Variations of genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which encode active fragments may be obtained using a variety of restriction enzymes. Proteases may be used to directly obtain active fragments of these toxins.

Equivalent toxins and/orgenes encoding these equivalent toxins can be derived from B.t. isolates and/or DNA libraries using the teachings provided herein. There are a number of methods for obtaining the pesticidal toxins of the instant invention. For example, antibodies to the pesticidal toxins disclosed and claimed herein can be used to identify and isolate other toxins from a mixture of proteins. Specifically, antibodies may be raised to the portions of the toxins which are most constant and most distinct from other B.t. toxins. These antibodies can then be used to specifically identify equivalent toxins with the characteristic activity by immunoprecipitation, enzyme linked immunosorbent assay (ELISA), or Western blotting. Antibodies to the toxins disclosed herein, or to equivalent toxins, or fragments of these toxins, can readily be prepared using standard procedures in this art. The genes which encode these toxins can then be obtained from the microorganism.

Fragments and equivalents which retain the pesticidal activity of the exemplified toxins would be within the scope of the subject invention. Also, because of the redundancy of the genetic code, a variety of different DNA sequences can encode the amino acid sequences disclosed herein. It is well within the skill of a person trained in the art to create these alternative DNA sequences encoding the same, or essentially the same, toxins. These variant DNA sequences are within the scope of the subject invention. As used herein, reference to "essentially the same" sequence refers to sequences which have amino acid substitutions, deletions, additions, or insertions which do not materially affect pesticidal activity. Fragments retaining pesticidal activity are also included in this definition.

A further method for identifying the toxins and genes of the subject invention is through the use of oligonucleotide probes. These probes are detectable nucleotide sequences. Probes provide a rapid method for identifying toxin-encoding genes of the subject invention. The nucleotide segments which are used as probes according to the invention can be synthesized using a DNA or RNA synthesizer and standard procedures. The probe will normally have at least about 10 bases, more usually at least about 18 bases, and may have up to about 50 bases or more, usually not having more than about 200 bases if the probe is made synthetically. However, longer probes can readily be utilized, and such probes can be, for example, several kilobases in length. The probe sequence is designed to be at least substantially complementary to a gene encoding a toxin of interest. The probe need not have perfect complementarity to the sequence to which it hybridizes. The probes may be labelled utilizing techniques which are well known to those skilled in this art. Such a probe analysis provides a rapid method for identifying potentially commercially valuable insecticidal endotoxin genes within the multifarious subspecies of B.t.

Various degrees of stringency of hybridization can be employed. The more stringent the conditions, the greater the complementarity that is required for duplex formation. Severity can be controlled by temperature, probe concentration, probe length, ionic strength, time, and the like. Preferably, hybridization is conducted under stringent conditions by techniques well known in the art, as described, for example, in Keller, G. H., M. M. Manak (1987) DNA Probes, Stockton Press, New York, N.Y., pp. 169–170. Low-stringency hybridization is the preferred method when a larger gene fragment is used.

As used herein "stringent" conditions for hybridization refers to conditions which achieve the same, or about the same, degree of specificity of hybridization as the conditions employed by the current applicants. Specifically, hybridization of immobilized DNA on Southern blots with 32P-labeled gene-specific probes was performed by standard methods (Maniatis, T., E. F. Fritsch, J. Sambrook [1982] Molecular Cloning: A Laboratory Manual, Cold Spring Harbor Laboratory, Cold Spring Harbor, N.Y.). In general, hybridization and subsequent washes were carried out under stringent conditions that allowed for detection of target sequences with homology to the exemplified toxin genes. For double-stranded DNA gene probes, hybridization was carried out overnight at 20°–25° C. below the melting temperature (Tm) of the DNA hybrid in 6X SSPE, 5X Denhardt's solution, 0.1% SDS, 0.1 mg/ml denatured DNA. The melting temperature is described by the following formula (Beltz, G. A., K. A. Jacobs, T. H. Eickbush, P. T. Cherbas, and F. C. Kafatos [1983] Methods of Enzymology, R. Wu, L. Grossman and K. Moldave [eds.] Academic Press, New York 100:266–285).

Tm=81.5° C+16.6 Log[Na+]+0.41(% G+C)-0.61(% formamide)-600/length of duplex in base pairs.

Washes are typically carried out as follows:

(1) Twice at room temperature for 15 minutes in 1X SSPE, 0.1% SDS (low stringency wash).

(2) Once at Tm-20° C. for 15 minutes in 0.2X SSPE, 0.1% SDS (moderate stringency wash).

For oligonucleotide probes, hybridization was carried out overnight at 10°–20° C. below the melting temperature (Tm) of the hybrid in 6X SSPE, 5X Denhardt's solution, 0.1% SDS, 0.1 mg/rnl denatured DNA. Tm for oligonucleotide probes can be determined by the "nearest-neighbor" method. See Breslaueretal., "PredictingDNA duplex stability from the base sequence," Proc. Natl. Acad. Sci. USA, 83 (11): 3746–3750 (June 1986); Rychlik and Rhoads, "A computerprogram for choosing optimal oligonucleotidesfor filter hybridization, sequencing and in vitro amplification of DNA," Nucleic Acids Res., 17 (21): 8543–8551 (Nov. 11, 1989); SantaLucia et al., "Improved nearest-neighbor parameters for predicting DNA duplex stability," Biochemistry 35 (11): 3555–3562 (Mar. 19, 1996); Doktycz et al., "Optical melting of 128 octamer DNA duplexes. Effects of base pair location and nearest neighbors on thermal stability," J Biol Chem., 270 (15): 8439–8445 (Apr. 14, 1995). Alternatively, the Tm can be determined by the following formula:

Tm (° C.)=2(number T/A base pairs) +4(number G/C base pairs) (Suggs, S. V., T. Miyake, E. H. Kawashime, M. J. Johnson, K. Itakura, and R. B. Wallace [1981] ICN-UCLA Symp. Dev. Biol. Using Purified Genes, D. D. Brown [ed.], Academic Press, New York, 23:683–693).

Washes were typically carried out as follows:

(1) Twice at room temperature for 15 minutes 1X SSPE, 0.1% SDS (low stringency wash).

(2) Once at the hybridizationtemperaturefor 15 minutes in 1X SSPE, 0.1% SDS (moderate stringency wash).

The DNA sequences of the subject invention can also be used as primers for PCR amplification. Polymerase Chain Reaction (PCR) is a repetitive, enzymatic, primed synthesis of a nucleic acid sequence. This procedure is well known and commonly used by those skilled in this art (see Mullis, U.S. Pat. Nos. 4,683,195, 4,683,202, and 4,800,159; Saiki, Randall K., Stephen Scharf, Fred Faloona, Kary B. Mullis, Glenn T. Horn, Henry A. Erlich, Norman Arnheim [1985] "Enzymatic Amplification of P-Globin Genomic Sequences and Restriction Site Analysis for Diagnosis of Sickle Cell Anemia," Science 230:1350–1354.). PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. Since the extension product of each primer can serve as a template for the other primer, each cycle essentially doubles the amount of DNA fragment produced in the previous cycle. This results in the exponential accumulation of the specific target fragment, up to several million-fold in a few hours. By using a thermostable DNA polymerase such as Taq polymerase, which is isolated from the thermophilic bacterium Thermus aquaticus, the amplification process can be completely automated.

Certain toxins of the subject invention have been specifically exemplified herein. Since these toxins are merely exemplary of the toxins of the subject invention, it should be readily apparent that the subject invention comprises variant or equivalent toxins (and nucleotide sequences coding for equivalent toxins) having the same or similar pesticidal activity of the exemplified toxin. Equivalent toxins will have high amino acid homology with an exemplified toxin. This amino acid identity will typically be greater than 60%, preferably be greater than 75%, more preferably greater than 80%, more preferably greater than 90%, and can be greater than 95%. These identities are as determined using standard alignment techniques. The amino acid homology will be highest in critical regions of the toxin which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. Table 1 provides a listing of examples of amino acids belonging to each class.

TABLE 1

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin.

As used herein, reference to "isolated" polynucleotides and/or "purified" toxins refers to these molecules when they are not associated with the other molecules with which they would be found in nature. Thus, reference to "isolated and purified" signifies the involvement of the "hand of man" as described herein.

Recombinant hosts. The toxin-encoding genes of the subject invention can be introduced into a wide variety of microbial or plant hosts. Expression of the toxin gene results, directly or indirectly, in the intracellular production and maintenance of the pesticide. With suitable microbial hosts, e.g., Pseudomonas, the microbes can be applied to the situs of the pest, where they will proliferate and be ingested. The result is a control of the pest. Alternatively, the microbe hosting the toxin gene can be treated under conditions that prolong the activity of the toxin and stabilize the cell. The treated cell, which retains the toxic activity, then can be applied to the environment of the target pest.

Where the B.t. toxin gene is introduced via a suitable vector into a microbialhost, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from enviromnental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera *Pseudomonas, Erwinia, Serratia, Kiebsiella, Xanthomonas, Streptomyces, Rhizobium, Rhodopseudomonas, Methylophilus, Agrobacterium, Acetobacter, Lactobacillus, Arthrobacter, Azotobacter, Leuconostoc,* and *Alcaligenes;* fungi, particularly yeast, e.g., genera *Saccharomyces, Cryptococcus, Kluyveromyces, Sporobolomyces, Rhodotorula, and Aureobasidium.* Of particular interest are such phytosphere bacterial species as *Pseudomonassyringae, Pseudomonasfluorescens, Serratia marcescens, Acetobacterxylinum, Agrobacteriumtumefaciens, Rhodopseudomonas spheroides, Xanthomonas campestris, Rhizobium meliloti, Alcaligenes eutrophus,* and *Azotobacter vinlandii;* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pullulans.* Of particular interest are the pigmented microorganisms.

A significant number of methods are available for introducing a B.t. gene encoding a toxin into a microorganism host under conditions which allow for stable maintenance and expression of the gene. These methods are well known to those skilled in the art and are described, for example, in U.S. Pat. No. 5,135,867, which is incorporated herein by reference.

Control of coleopterans, including corn rootworm, as well as nematodes, using the isolates, toxins, and genes of the subject invention can be accomplished by a variety of methods known to those skilled in the art. These methods include, for example, the application of B.t. isolates to the pests (or their location), the application of recombinant microbes to the pests (or their locations), and the transformation of plants with genes which encode the pesticidal toxins of the subject invention. Recombinant microbes may be, for example, a B.t., *E. coli,* or *Pseudomonas.* Transformations can be made by those skilled in the art using standard techniques. Materials necessary for these transformations are disclosed herein or are otherwise readily available to the skilled artisan.

Synthetic genes which are functionally equivalent to the genes exemplified herein can also be used to transform hosts. Methods for the production of synthetic genes can be found in, for example, U.S. Pat. No. 5,380,831.

Treatment of cells. As mentioned above, B.t. or recombinant cells expressing a B.t. toxin can be treated to prolong the toxin activity and stabilize the cell. The pesticide microcapsule that is formed comprises the B.t. toxin within a cellular structure that has been stabilized and will protect the toxin when the microcapsule is applied to the environment of the target pest. Suitable host cells may include either prokaryotes or eukaryotes, normally being limited to those cells which do not produce substances toxic to higher organisms, such as mammals. However, organisms which produce substances toxic to higher organisms could be used, where the toxic substances are unstable or the level of application sufficiently low as to avoid any possibility of toxicity to a mammalian host. As hosts, of particular interest will be the prokaryotes and the lower eukaryotes, such as fungi.

The cell will usually be intact and be substantially in the proliferative form when treated, rather than in a spore form, although in some instances spores may be employed.

Treatment of the microbial cell, e.g., a microbe containing the B.t. toxin gene, can be by chemical or physical means, or by a combination of chemical and/or physical means, so long as the technique does not deleteriously affect the properties of the toxin, nor diminish the cellular capability of protecting the toxin. Examples of chemical reagents are halogenating agents, particularly halogens of atomic no. 17–80. More particularly, iodine can be used under mild conditions and for sufficient time to achieve the desired results. Other suitable techniques include treatment with aldehydes, such as glutaraldehyde; anti-infectives, such as zephiran chloride and cetylpyridinium chloride; alcohols, such as isopropyl and ethanol; various histologic fixatives, such as Lugol iodine, Bouin's fixative, various acids and Helly's fixative (See: Humason, Gretchen L., Animal Tissue Techniques, W. H. Freeman and Company, 1967); or a combination of physical (heat) and chemical agents that preserve and prolong the activity of the toxin produced in the cell when the cell is administered to the host environment. Examples of physical means are short wavelength radiation such as gamma-radiation and X-radiation, freezing, UV irradiation, lyophilization, and the like. Methods for treatment of microbial cells are disclosed in U.S. Pat. Nos. 4,695,455 and 4,695,462, which are incorporated herein by reference.

The cells generally will have enhanced structural stability which will enhance resistance to environmental conditions. Where the pesticide is in a proform, the method of cell treatment should be selected so as not to inhibit processing of the proform to the mature form of the pesticide by the target pest pathogen. For example, formaldehyde will crosslink proteins and could inhibit processing of the proform of a polypeptide pesticide. The method of treatment should retain at least a substantial portion of the bioavailability or bioactivity of the toxin.

Characteristics of particular interest in selecting a host cell for purposes of production include ease of introducing the B.t. gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; survival in aqueous environments; lack of mammalian toxicity; attractiveness to pests for ingestion; ease of killing and fixing without damage to the toxin; and the like. Other considerations include ease of formulation and handling, economics, storage stability, and the like.

Growth of cells. The cellular host containing the B.t. insecticidal gene may be grown in any convenient nutrient medium, where the DNA construct provides a selective advantage, providing for a selective medium so that substantially all or all of the cells retain the B.t. gene. These cells may then be harvested in accordance with conventional ways. Alternatively, the cells can be treated prior to harvesting.

The B.t. cells of the invention can be cultured using standard art media and fermentation techniques. Upon completion of the fermentation cycle the bacteria can be harvested by first separating the B.t. spores and crystals from the fermentation broth by means well known in the art. The recovered B.t. spores and crystals can be formulated into a wettable powder, liquid concentrate, granules or other formulations by the addition of surfactants, dispersants, inert carriers, and other components to facilitate handling and application for particular target pests. These formulations and application procedures are all well known in the art.

Methods and formulations for control of pests. Control of coleopterans using the toxins and genes of the subject invention can be accomplished by a variety of methods known to those skilled in the art. These methods include, for example, the application of B.t. isolates to the pests (or their location), the application of recombinant microbes to the pests (or their locations), and the transformation of plants with genes which encode the pesticidal toxins of the subject invention. Recombinant microbes may be, for example, a B.t., *E. coli,* or Pseudomonas. Transformations can be made by those skilled in the art using standard techniques. Materials necessary for these transformations are disclosed herein or are otherwise readily available to the skilled artisan.

Formulated bait granules containing an attractant and spores and crystals of the B.t. isolates, or recombinant microbes comprising the genes obtainable from the B.t. isolates disclosed herein, can be applied to the soil. Formulated product can also be applied as a seed-coating or root treatment or total plant treatment at later stages of the crop cycle. Plant and soil treatments of B.t. cells may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include Theological agents, surfactants, emulsifiers, dispersants, or polymers.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the pest, e.g., soil and foliage, by spraying, dusting, sprinkling, or the like.

All of the U.S. Patents referred to herein are hereby incorporated by reference.

Following are examples which illustrate procedures for practicing the invention. These examples should not be construed as limiting. All percentages are by weight and all solvent mixture proportions are by volume unless otherwise noted.

EXAMPLE 1

Culturing B.t. Isolates

A subculture of the B.t. isolate can be used to inoculate the following medium, a peptone, glucose, salts medium.

| | |
|---|---|
| Bacto Peptone | 7.5 g/l |
| Glucose | 1.0 g/l |
| $KH_2PO_4$ | 3.4 g/l |
| $K_2HPO_4$ | 4.35 g/l |
| Salts Solution | 5.0 ml/l |
| $CaCl_2$ Solution | 5.0 ml/l |
| Salts Solution (100 ml) | |
| $MgSO_4.7H_2O$ | 2.46 g |
| $MnSO_4.H_2O$ | 0.04 g |
| $ZnSO_4.7H_2O$ | 0.28 g |
| $FeSO_4.7H_2O$ | 0.40 g |
| $CaCl_2$ Solution (100) ml) | |
| $CaCl_2.2H_2O$ | 3.66 g |
| pH 7.2 | |

The salts solution and $CaCl_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The B.t. spores and crystals, obtained in the above fermentation, can be isolated by procedures well known in the art. A frequently-used procedure is to subject the harvested fermentation broth to separation techniques, e.g., centrifugation.

EXAMPLE 2

Expression and Purification of Recombinant Cry6A Toxin from Strain PS86A 1

Starter culture was prepared consisting of 50 ml of autoclaved LB medium contained in a 250-ml baffled culture flask, inoculated with 50 μl of PS86A1. The flask was closed and incubated at 30° C. on a rotary shaker at 225 rpm for 4–6 hours. Five milliliters of the starter was then used to inoculate 300 ml of autoclaved growth medium in a 2-liter baffled culture flask with foam plugs. The growth medium is designated NYS-CAA and consists of:

| | | |
|---|---|---|
| Nutrient broth (Difco) | 3.75 | g |
| Tryptone | 3.75 | g |
| Casamino acids | 6.00 | g |
| Yeast extract | 1.50 | g |
| B.t. salts | 30 | ml |

The *B.t.* salts stock solution consists of:

| | | |
|---|---|---|
| $CaCl_2.2H_2O$ | 10.30 | g |
| $MgCl_2.6H_2O$ | 20.35 | g |
| $MnCl_2.4H_2O$ | 1.00 | g |
| $FeSO_4.7H_2O$ | 0.02 | g |
| $ZnSO_4.7H_2O$ | 0.02 | g |
| $(NH_4)_2SO_4$ | 0.02 | g |
| HCl(7N) | 1.00 | ml |

The inoculated culture was grown on a large rotary shaker at 30° C. for up to 65 hours or more (until lysis is substantially complete). The particulates were harvested by centrifugation at 4° C. and 8,000 rpm in a Sorvall GS-3 rotor. The resulting pellet was washed three times with approximately 5 volumes of distilled water by resuspending the pelleted material and centrifuging as described. Toxin crystals were purified using centrifugation (100 minutes at 6,500 rpm in a Sorval HS-4 rotor at 4° C.) over sodium bromide step gradients consisting of 15 ml 50%, 7 ml of 45%, and 7 ml of 40% NaBr. Crystals were removed from the gradients, diluted approximately 50% with distilled water, and concentrated by centrifngation at 14,000 rpm at 4° C. in a Sorvall SS-34 rotor. The crystal protein pellet was suspended in a minimal amount of distilled water, quick frozen in a dry ice/isopropanol bath, and stored at −80° C. SDS-PAGE analysis of the products of this process reveals a dominant 54 kDa Coomassie staining band. Analysis by mass spectroscopy (matrix-assisted laser desorbtion-time of flight, MALDI-TOF) of the protein detects a dominant peak at 54,080 daltons. The molecular weight calculated from the amino acid sequence of the intact 86A1 toxin is 54,080 daltons.

EXAMPLE 3

Proteolytic Digestion of Cry6A Toxin

The crystal proteins obtained as above were proteolytically digested using bovine trypsin. The digestion mixture contained 133 mM Tris base, 1 M urea, 5 mg of 86A1 toxin protein, 50 μg of trypsin (e.g., Sigma Type XIII or Boerhinger-Mannheim sequencing grade), in 2.0 ml final volume. The above mixture minus trypsin was incubated at 37° C. for 15 minutes. Trypsin, as a 1 mg/ml solution in 10 mM sodium acetate, pH 4.5, was then added and allowed to incubate an additional two hours at 37° C. At the conclusion of the incubation, the reaction mixture was centrifuged for 15 minutes in an Eppendorf centrifuge at 4° C. The supernatant was removed and placed in a 2-ml Centricon 30 (Amicon) and washed three times with 2 ml of distilled water. The washed sample was stored at 4° C. or was quick frozen in a dry ice/isopropanol bath and stored at −80° C.

SDS-PAGE analysis of the washed digestion mixture reveals a dominant Coomassie staining band at 45,000 daltons, with minor bands detectable at 46,000 and daltons and approximately 34,000 daltons. MALDI-TOF reveals a single band at 46,500 daltons. Amino terminal sequence analysis using automated (ABI) Edman degradation of the SDS-PAGE band blotted to a PVDF membrane, reveals an 11-amino acid sequence which corresponds to the known sequence of the full-length 86A1 toxin (SEQ ID NO. 2) starting at amino acid residue number 11. Automated carboxyl terminal sequencing (HP) of the major SDS-PAGE band blotted to a Zitex membrane revealed a sequence which corresponds to the known sequence of 86A1 toxin beginning at amino acid residue 441 and ending at amino acid residue 443 of SEQ ID NO.2. The calculated mass of the sequenced fragment (residue 12–443) is 48,725 daltons.

This resulting tuncated toxin is referred to herein as R443, the tuncated 86A1 toxin, or the truncated Cry6A toxin. The sequence of this toxin was determined to be that of SEQ ID NO. 6. See also SEQ ID NO. 5.

In addition to the above preferred method, a similar result can be obtained in the absence of 1 M urea. If 140 mM β-mercaptoethanol is added, either in the presence or absence of 1 M urea, the yield of product is much reduced. This can be overcome, to some extent, in the absence of urea by increasing the amount of trypsin 10-fold. It is likely that any buffer having a pH between pH 9–11 would perform similarly.

EXAMPLE 4

Western Corn Rootworm Bioassay

The truncated protein preparations obtained as described above in Example 3 were bioassayed against western corn rootworm and were found to have significant toxin activity.

As shown in Table 2, the levels of activity obtained by using the truncated 86A1 protein unexpectedly exceed the control levels obtained by using the full length 86A1 protein.

TABLE 2

| | | MORTALITY | | |
|---|---|---|---|---|
| Treatment | Dosage (μg/cm²) | Test 1 dead/total | Test 2 dead/total | Average % |
| Truncated 86A1 activated protein | 475 | 10/10 | 6/7 | 93 |
| | 237 | 7/10 | 10/10 | 85 |
| | 118 | 6/10 | 9/11 | 71 |
| | 59 | 0/10 | 5/11 | 23 |
| | 29 | 6/16 | 2/16 | 25 |
| Full length 86A1 protein | 481 | 1/16 | 3/13 | 14 |
| | 240 | 3/13 | 4/12 | 28 |
| | 120 | 4/24 | 1/12 | 12 |
| | 60 | 1/13 | 0/10 | 3 |
| | 30 | 6/24 | 2/16 | 18 |
| Buffer control | 1X | 0/8 | 0/9 | 0 |
| | 0.5X | 1/8 | 0/11 | 6 |
| | 0.25X | 3/8 | 0/11 | 18 |
| | 0.12X | 0/11 | 0/10 | 0 |
| | 0.06X | 6/23 | 0/12 | 13 |

The LC50(μg/cm²) was determined for the original length (58kDa) 86A1 protein and for the truncated form (45 kDa) of the 86A1 protein. The results are reported in Table 3.

TABLE 3

| Protein | Process | Size of protein | LC50 μg/cm² |
|---|---|---|---|
| 86A1 | purified solubilized | 58 kDa | not lethal |
| 86A1 | purified solubilized trypsin digested | 45 kDa | 77 |

EXAMPLE 5

Construction of Fusion Proteins and Genes

A fusion protein consisting of Cry6B and Cry6A having activity against western corn rootworm can be constructed. It should be noted that the Cry6B/69D1 protein was not previously known to be useful for controlling corn rootworm. The sequence of the fall length Cry6B toxin obtainable from PS69D1 corresponds to SEQ ID NO.10. See also SEQ ID NO. 9.

The fusion consists of a gene segment from Cry6B joined to one from Cry6A such that the open reading frame is maintained. One embodiment consists of joining amino acids 1 through 394 of Cry6B to amino acids 386 through 443 of Cry6A. It would be preferable to make a crossover between the two genes at a point where there is substantial homology, because substantial homology infers similar three-dimensional structure and the possibility of fewer detrimental perturbations in three-dimensional structure. FIG. 1 is an alignment of Cry6A to Cry6B showing regions of homology for crossovers. Other possible examples of crossover points for gene fusions are shown below in Table 2. The table is not to be construed as limiting.

TABLE 4

| Cry6B amino acids | Cry6A amino acids |
|---|---|
| 1–394 | 386–443 |
| 1–248 | 241–443 |
| 1–264 | 256–443 |
| 1–302 | 295–443 |
| 1–395 | 387–443 |

Additionally, the constructs may be truncated on the amino terminus so that the first approximately 10–25 amino acids may be absent.

EXAMPLE 6

Insertion of Toxin Genes Into Plants

One aspect of the subject invention is the transformation of plants with the subject genes encoding the insecticidal toxin. The transformed plants are resistant to attack by the target pest. In preferred embodiments, the truncated genes of the subject invention are optimized for use in plants. SEQ ID NOS. 3 and 4 provide sequence information for plant-optimized versions of the full-length cry6A gene and toxin. The truncated genes can also be optimized for use in plants. For example, the gene and toxin sequences of SEQ ID NOS. 7 and 8, which can also be referred to as R390, are optimized for use in plants.

Genes encoding pesticidal toxins, as disclosed herein, can be inserted into plant cells using a variety of techniques which are well known in the art. For example, a large number of cloning vectors comprising a replication system in *E. coli* and a marker that permits selection of the transformed cells are available for preparation for the insertion of foreign genes into higher plants. The vectors comprise, for example, pBR322, pUC series, M13mp series, pACYC 184, etc. Accordingly, the sequence encoding the B.t. toxin can be inserted into the vector at a suitable restriction site. The resulting plasmid is used for transformation into *E. coli.* The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted.

The use of T-DNA for the transformation of plant cells has been intensively researched and sufficiently described in EP 120 516; Hoekema(1985) In: The Binary Plant Vector System, Offset-durkkerij Kanters B. V., Alblasserdam, Chapter 5; Fraley et al., Crit. Rev. Plant Sci. 4:1–46; and An et al. (1985) EMBO J 4:277–287.

Once the inserted DNA has been integrated in the genome, it is relatively stable there and, as a rule, does not come out again. It normally contains a selection marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA.

A large number of techniques are available for inserting DNA into a plant host cell. Those techniques include transformation with T-DNA using *Agrobacterium tumefaciens* or *Agrobacterium rhizogenes* as transformation agent, fusion, injection, biolistics (microparticle bombardment), or electroporation as well as other possible methods. If Agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in Agrobacteria. The intermediate vector can be transferred into Agrobacterium tumefaciens by means of a helper plasmid (conjugation). Binary vectors can replicate themselves both in *E. coli* and in Agrobacteria. They comprise a selection marker gene and a linker or polylinker which are framed by the right and left T-DNA border regions. They can be transformed directly into Agrobacteria (Holsters etal. [1978] Mol. Gen. Genet. 163:181–187). The Agrobacterium used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

In a preferred embodiment of the subject invention, plants will be transformed with genes wherein the codon usage has been optimized for plants. See, for example, U.S. Pat. No. 5,380,831. Also, advantageously, plants encoding a truncated toxin will be used. The truncated toxin typically will encode about 55% to about 80% of the full length toxin. Methods for creating synthetic B.t. genes for use in plants are known in the art.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A polynucleotide sequence which encodes a *Bacillus thuringiensis* Cry6A toxin for controlling coleopterans, wherein said toxin is truncated compared to the full length toxin as it is naturally expressed, wherein said toxin has the amino acid sequence of SEQ ID NO. 6.

2. A recombinant host transformed with a polynucleotide sequence of claim 1.

3. The recombinant host, according to claim 2, wherein said transformed host is a microbe.

4. The recombinant host, according to claim 2, wherein said microbe is selected from the group consisting of *Escherichia coli* and *Pseudomonas.*

5. The recombinant host, according to claim 3, wherein said transformed host is a plant.

6. A polynucleotide sequence which encodes a toxin having activity against coleopteran insects, wherein said polynucleotide sequence has the nucleotide sequence of SEQ ID NO. 3, or fragments thereof.

7. A recombinant DNA transfer vector comprising a polynucleotide sequence which encodes a toxin having activity against coleopteran insects, wherein said polynucleotide sequence has the nucleotide sequence of SEQ ID NO. 3, or fragments thereof.

8. A recombinant plant host transformed with a polynucleotide sequence which encodes a toxin having activity against coleopteran insects, wherein said polynucleotide sequence has the nucleotide sequence of SEQ ID NO. 3, or fragments thereof.

* * * * *

UNITED STATES PATENT AND TRADEMARK OFFICE

CERTIFICATE OF CORRECTION

PATENT NO. : 5,874,288

DATED : February 23, 1999

INVENTOR(S) : Mark Thompson, et. al.

It is certified that error appears in the above-identified patent and that said Letters Patent is hereby corrected as shown below:

Column 1, line 60: “insecticideuse” should read --insecticide use--.

Column 2, line 39: “Bennimidazole” should read --benzimidazole--.

Column 3, line 58: “beenproposed” should read --been proposed--; and line 64: “cyta” should read --cytA--.

line 53: “Isolates” should read --isolates--.

Column 5, lines 13-14: “Proteolysistrims” should read --Proteolysis trims--; and line 36: “farther” should read --further--.

Column 6, line 9: “fill” should read --full--; and line 19: “fill” should read --full--.

Column 8, line 10: “and/orgenes” should read --and/or genes--.

Column 10, line 6: “P-Globin” should read --β-Globin--.

UNITED STATES PATENT AND TRADEMARK OFFICE

CERTIFICATE OF CORRECTION

PATENT NO. : 5,874,288

DATED : February 23, 1999

INVENTOR(S) : Mark Thompson, et. al.

It is certified that error appears in the above-identified patent and that said Letters Patent is hereby corrected as shown below:

Column 11, line 20: "microbialhost" should read --microbial host--;

line 37: "*Kiebsiella*" should read --*Klebsiella*--;

line 46: "*Pseudomonassyringae*" should read --*Pseudomonas syringae*--;

line 46: "*pseudomonasfluorescens*" should read --*Pseudomonas fluorescens*--; and line 47: "*Acetobacterxylinum*" should read --*Acetobacter xylinum*--.

Column 13, line 64: "Theological" should read --rheological--.

Column 16, line 8: "tuncated" should read --truncated--; and line 9: "tuncated" should read --truncated--.

Column 17, line 1: "fall" should read --full--.

Column 18, line 36: "etal." should read --*et al.*--.

Signed and Sealed this

Twenty-fourth Day of August, 1999

Attest:

Q. TODD DICKINSON

Attesting Officer

*Acting Commissioner of Patents and Trademarks*

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
( A ) LENGTH: 1425 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: BACILLUS THURINGIENSIS
( C ) INDIVIDUAL ISOLATE: PS86A1

( v i i ) IMMEDIATE SOURCE:
( A ) LIBRARY: E. coli NM522[pMYC2320]

( i x ) FEATURE:
( A ) NAME/KEY: mat_peptide
( B ) LOCATION: 1..1425

( x i ) SEQUENCE DESCRIPTION: SEQ ID NO:1:

```
ATGATTATTG ATAGTAAAAC GACTTTACCT AGACATTCAC TTATTCATAC AATTAAATTA   60
AATTCTAATA AGAAATATGG TCCTGGTGAT ATGACTAATG GAAATCAATT TATTATTTCA  120
AAACAAGAAT GGGCTACGAT TGGAGCATAT ATTCAGACTG GATTAGGTTT ACCAGTAAAT  180
GAACAACAAT TAAGAACACA TGTTAATTTA AGTCAGGATA TATCAATACC TAGTGATTTT  240
TCTCAATTAT ATGATGTTTA TTGTTCTGAT AAAACTTCAG CAGAATGGTG GAATAAAAAT  300
TTATATCCTT TAATTATTAA ATCTGCTAAT GATATTGCTT CATATGGTTT TAAAGTTGCT  360
GGTGATCCTT CTATTAAGAA AGATGGATAT TTTAAAAAAT TGCAAGATGA ATTAGATAAT  420
ATTGTTGATA ATAATTCCGA TGATGATGCA ATAGCTAAAG CTATTAAAGA TTTTAAAGCG  480
CGATGTGGTA TTTTAATTAA AGAAGCTAAA CAATATGAAG AAGCTGCAAA AAATATTGTA  540
ACATCTTTAG ATCAATTTTT ACATGGTGAT CAGAAAAAAT TAGAAGGTGT TATCAATATT  600
CAAAAACGTT TAAAAGAAGT TCAAACAGCT CTTAATCAAG CCCATGGGGA AAGTAGTCCA  660
GCTCATAAAG AGTTATTAGA AAAAGTAAAA AATTTAAAAA CAACATTAGA AAGGACTATT  720
AAAGCTGAAC AAGATTTAGA GAAAAAAGTA GAATATAGTT TTCTATTAGG ACCATTGTTA  780
GGATTTGTTG TTTATGAAAT TCTTGAAAAT ACTGCTGTTC AGCATATAAA AAATCAAATT  840
GATGAGATAA AGAAACAATT AGATTCTGCT CAGCATGATT TGGATAGAGA TGTTAAAATT  900
ATAGGAATGT TAAATAGTAT TAATACAGAT ATTGATAATT TATATAGTCA AGGACAAGAA  960
GCAATTAAAG TTTTCCAAAA GTTACAAGGT ATTTGGGCTA CTATTGGAGC TCAAATAGAA 1020
AATCTTAGAA CAACGTCGTT ACAAGAAGTT CAAGATTCTG ATGATGCTGA TGAGATACAA 1080
ATTGAACTTG AGGACGCTTC TGATGCTTGG TTAGTTGTGG CTCAAGAAGC TCGTGATTTT 1140
ACACTAAATG CTTATTCAAC TAATAGTAGA CAAAATTTAC CGATTAATGT TATATCAGAT 1200
```

-continued

```
TCATGTAATT GTTCAACAAC AAATATGACA TCAAATCAAT ACAGTAATCC AACAACAAAT 1260

ATGACATCAA ATCAATATAT GATTTCACAT GAATATACAA GTTTACCAAA TAATTTTATG 1320

TTATCAAGAA ATAGTAATTT AGAATATAAA TGTCCTGAAA ATAATTTTAT GATATATTGG 1380

TATAATAATT CGGATTGGTA TAATAATTCG GATTGGTATA ATAAT                 1425
```

( 2 ) INFORMATION FOR SEQ ID NO:2:

( i ) SEQUENCE CHARACTERISTICS:
( A ) LENGTH: 475 amino acids
( B ) TYPE: amino acid
( C ) STRANDEDNESS: single
( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
( A ) ORGANISM: BACILLUS THURINGIENSIS
( C ) INDIVIDUAL ISOLATE: PS86A1

( i x ) FEATURE:
( A ) NAME/KEY: Protein
( B ) LOCATION: 1..475

( x i ) SEQUENCE DESCRIPTION: SEQ ID NO:2:

```
Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255
```

-continued

Gly Pro Leu Leu Gly Phe Val Val Tyr Glu Ile Leu Glu Asn Thr Ala
260 265 270

Val Gln His Ile Lys Asn Gln Ile Asp Glu Ile Lys Lys Gln Leu Asp
275 280 285

Ser Ala Gln His Asp Leu Asp Arg Asp Val Lys Ile Ile Gly Met Leu
290 295 300

Asn Ser Ile Asn Thr Asp Ile Asp Asn Leu Tyr Ser Gln Gly Gln Glu
305 310 315 320

Ala Ile Lys Val Phe Gln Lys Leu Gln Gly Ile Trp Ala Thr Ile Gly
325 330 335

Ala Gln Ile Glu Asn Leu Arg Thr Thr Ser Leu Gln Glu Val Gln Asp
340 345 350

Ser Asp Asp Ala Asp Glu Ile Gln Ile Glu Leu Glu Asp Ala Ser Asp
355 360 365

Ala Trp Leu Val Val Ala Gln Glu Ala Arg Asp Phe Thr Leu Asn Ala
370 375 380

Tyr Ser Thr Asn Ser Arg Gln Asn Leu Pro Ile Asn Val Ile Ser Asp
385 390 395 400

Ser Cys Asn Cys Ser Thr Thr Asn Met Thr Ser Asn Gln Tyr Ser Asn
405 410 415

Pro Thr Thr Asn Met Thr Ser Asn Gln Tyr Met Ile Ser His Glu Tyr
420 425 430

Thr Ser Leu Pro Asn Asn Phe Met Leu Ser Arg Asn Ser Asn Leu Glu
435 440 445

Tyr Lys Cys Pro Glu Asn Asn Phe Met Ile Tyr Trp Tyr Asn Asn Ser
450 455 460

Asp Trp Tyr Asn Asn Ser Asp Trp Tyr Asn Asn
465 470 475

( 2 ) INFORMATION FOR SEQ ID NO:3:

( i ) SEQUENCE CHARACTERISTICS:
( A ) LENGTH: 1428 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:3:

ATGGTCATTG ACAGCAAGAC GACTCTACCA CGGCACTCAC TGATTCACAC AATCAAGCTG 60

AACTCTAACA AGAAGTATGG TCCTGGCGAT ATGACTAACG GGAACCAGTT CATCATATCC 120

AAGCAAGAAT GGGCCACGAT TGGCGCATAC ATTCAGACTG GACTCGGCTT ACCAGTGAAT 180

GAGCAACAGC TGAGAACCCA CGTTAACCTT AGTCAAGACA TCAGCATACC ATCTGACTTT 240

TCTCAACTCT ACGATGTGTA TTGTTCTGAC AAGACTAGTG CAGAATGGTG GAACAAGAAT 300

CTCTATCCTT TGATCATCAA GTCTGCCAAT GACATTGCTT CATATGGTTT CAAAGTTGCT 360

GGTGATCCTT CGATCAAGAA AGATGGTTAC TTCAAGAAGC TTCAAGATGA ACTCGACAAC 420

ATTGTTGACA ACAACTCCGA CGACGATGCG ATAGCCAAAG CCATCAAGGA CTTCAAAGCA 480

AGATGTGGCA TTCTCATCAA GGAAGCCAAG CAGTATGAAG AAGCTGCCAA GAACATTGTA 540

ACATCATTGG ATCAGTTTCT CCATGGAGAC CAGAAGAAGC TCGAGGGTGT CATCAACATT 600

CAGAAACGTC TGAAAGAGGT TCAAACAGCT CTGAATCAAG CCCATGGGGA ATCCAGTCCA 660

GCTCACAAAG AGCTTCTTGA GAAAGTGAAG AACTTGAAGA CCACACTTGA GAGGACCATC 720

-continued

| | | | | | | |
|---|---|---|---|---|---|---|
| AAAGCTGAAC | AAGACTTGGA | GAAGAAAGTA | GAGTACAGCT | TTCTACTTGG | ACCCTTGTTA | 780 |
| GGCTTTGTTG | TCTACGAGAT | TCTTGAGAAC | ACTGCTGTTC | AACACATCAA | GAATCAAATC | 840 |
| GATGAGATCA | AGAAACAGTT | GGATTCTGCG | CAACATGACT | TGGATCGCGA | TGTGAAGATC | 900 |
| ATTGGAATGC | TCAACAGCAT | CAACACTGAC | ATTGACAACT | TGTATAGTCA | AGGACAAGAA | 960 |
| GCAATCAAAG | TCTTTCAGAA | GCTACAAGGG | ATATGGGCCA | CTATTGGAGC | TCAGATAGAG | 1020 |
| AATCTTCGCA | CCACGTCCCT | TCAAGAAGTC | CAAGACTCTG | ATGATGCTGA | TGAGATACAG | 1080 |
| ATTGAACTTG | AGGACGCATC | TGATGCATGG | TTAGTTGTGG | CTCAAGAAGC | TCGTGACTTC | 1140 |
| ACACTGAATG | CCTACTCAAC | CAACAGTCGA | CAGAATCTCC | CGATCAATGT | GATCTCAGAT | 1200 |
| TCATGCAATT | GCTCCACCAC | CAACATGACA | TCCAATCAGT | ACAGCAATCC | AACAACCAAC | 1260 |
| ATGACTAGCA | ATCAGTACAT | GATTAGCCAT | GAGTATACCA | GCTTGCCCAA | CAACTTCATG | 1320 |
| TTGTCAAGGA | ATTCGAACCT | GGAGTACAAG | TGCCCTGAGA | ACAACTTCAT | GATCTACTGG | 1380 |
| TACAACAACT | CCGATTGGTA | CAACAATTCG | GATTGGTACA | ACAATTAA | | 1428 |

( 2 ) INFORMATION FOR SEQ ID NO:4:

( i ) SEQUENCE CHARACTERISTICS:
( A ) LENGTH: 475 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:4:

| | | | | | | | | | | | | | | | |
|---|---|---|---|---|---|---|---|---|---|---|---|---|---|---|---|
| Met | Val | Ile | Asp | Ser | Lys | Thr | Thr | Leu | Pro | Arg | His | Ser | Leu | Ile | His |
| 1 | | | | 5 | | | | | 10 | | | | | 15 | |
| Thr | Ile | Lys | Leu | Asn | Ser | Asn | Lys | Lys | Tyr | Gly | Pro | Gly | Asp | Met | Thr |
| | | | 20 | | | | | 25 | | | | | 30 | | |
| Asn | Gly | Asn | Gln | Phe | Ile | Ile | Ser | Lys | Gln | Glu | Trp | Ala | Thr | Ile | Gly |
| | | 35 | | | | | 40 | | | | | 45 | | | |
| Ala | Tyr | Ile | Gln | Thr | Gly | Leu | Gly | Leu | Pro | Val | Asn | Glu | Gln | Gln | Leu |
| | 50 | | | | | 55 | | | | | 60 | | | | |
| Arg | Thr | His | Val | Asn | Leu | Ser | Gln | Asp | Ile | Ser | Ile | Pro | Ser | Asp | Phe |
| 65 | | | | | 70 | | | | | 75 | | | | | 80 |
| Ser | Gln | Leu | Tyr | Asp | Val | Tyr | Cys | Ser | Asp | Lys | Thr | Ser | Ala | Glu | Trp |
| | | | | 85 | | | | | 90 | | | | | 95 | |
| Trp | Asn | Lys | Asn | Leu | Tyr | Pro | Leu | Ile | Ile | Lys | Ser | Ala | Asn | Asp | Ile |
| | | | 100 | | | | | 105 | | | | | 110 | | |
| Ala | Ser | Tyr | Gly | Phe | Lys | Val | Ala | Gly | Asp | Pro | Ser | Ile | Lys | Lys | Asp |
| | | 115 | | | | | 120 | | | | | 125 | | | |
| Gly | Tyr | Phe | Lys | Lys | Leu | Gln | Asp | Glu | Leu | Asp | Asn | Ile | Val | Asp | Asn |
| | 130 | | | | | 135 | | | | | 140 | | | | |
| Asn | Ser | Asp | Asp | Asp | Ala | Ile | Ala | Lys | Ala | Ile | Lys | Asp | Phe | Lys | Ala |
| 145 | | | | | 150 | | | | | 155 | | | | | 160 |
| Arg | Cys | Gly | Ile | Leu | Ile | Lys | Glu | Ala | Lys | Gln | Tyr | Glu | Glu | Ala | Ala |
| | | | | 165 | | | | | 170 | | | | | 175 | |
| Lys | Asn | Ile | Val | Thr | Ser | Leu | Asp | Gln | Phe | Leu | His | Gly | Asp | Gln | Lys |
| | | | 180 | | | | | 185 | | | | | 190 | | |
| Lys | Leu | Glu | Gly | Val | Ile | Asn | Ile | Gln | Lys | Arg | Leu | Lys | Glu | Val | Gln |
| | | 195 | | | | | 200 | | | | | 205 | | | |
| Thr | Ala | Leu | Asn | Gln | Ala | His | Gly | Glu | Ser | Ser | Pro | Ala | His | Lys | Glu |
| | 210 | | | | | 215 | | | | | 220 | | | | |
| Leu | Leu | Glu | Lys | Val | Lys | Asn | Leu | Lys | Thr | Thr | Leu | Glu | Arg | Thr | Ile |

-continued

```
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Thr Asn Ser Arg Gln Asn Leu Pro Ile Asn Val Ile Ser Asp
385                 390                 395                 400

Ser Cys Asn Cys Ser Thr Thr Asn Met Thr Ser Asn Gln Tyr Ser Asn
                405                 410                 415

Pro Thr Thr Asn Met Thr Ser Asn Gln Tyr Met Ile Ser His Glu Tyr
            420                 425                 430

Thr Ser Leu Pro Asn Asn Phe Met Leu Ser Arg Asn Ser Asn Leu Glu
        435                 440                 445

Tyr Lys Cys Pro Glu Asn Asn Phe Met Ile Tyr Trp Tyr Asn Asn Ser
    450                 455                 460

Asp Trp Tyr Asn Asn Ser Asp Trp Tyr Asn Asn
465                 470                 475
```

( 2 ) INFORMATION FOR SEQ ID NO:5:

( i ) SEQUENCE CHARACTERISTICS:
( A ) LENGTH: 1299 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:5:

```
ATGGGTCTGA TTCACACAAT CAAGCTGAAC TCTAACAAGA AGTATGGTCC TGGCGATATG   60
ACTAACGGGA ACCAGTTCAT CATATCCAAG CAAGAATGGG CCACGATTGG CGCATACATT  120
CAGACTGGAC TCGGCTTACC AGTGAATGAG CAACAGCTGA GAACCCACGT TAACCTTAGT  180
CAAGACATCA GCATACCATC TGACTTTTCT CAACTCTACG ATGTGTATTG TTCTGACAAG  240
ACTAGTGCAG AATGGTGGAA CAAGAATCTC TATCCTTTGA TCATCAAGTC TGCCAATGAC  300
ATTGCTTCAT ATGGTTTCAA AGTTGCTGGT GATCCTTCGA TCAAGAAAGA TGGTTACTTC  360
AAGAAGCTTC AAGATGAACT CGACAACATT GTTGACAACA ACTCCGACGA CGATGCGATA  420
GCCAAAGCCA TCAAGGACTT CAAAGCAAGA TGTGGCATTC TCATCAAGGA AGCCAAGCAG  480
TATGAAGAAG CTGCCAAGAA CATTGTAACA TCATTGGATC AGTTTCTCCA TGGAGACCAG  540
AAGAAGCTCG AGGGTGTCAT CAACATTCAG AAACGTCTGA AAGAGGTTCA AACAGCTCTG  600
```

-continued

AATCAAGCCC ATGGGGAATC CAGTCCAGCT CACAAAGAGC TTCTTGAGAA AGTGAAGAAC 660

TTGAAGACCA CACTTGAGAG GACCATCAAA GCTGAACAAG ACTTGGAGAA GAAAGTAGAG 720

TACAGCTTTC TACTTGGACC CTTGTTAGGC TTTGTTGTCT ACGAGATTCT TGAGAACACT 780

GCTGTTCAAC ACATCAAGAA TCAAATCGAT GAGATCAAGA AACAGTTGGA TTCTGCGCAA 840

CATGACTTGG ATCGCGATGT GAAGATCATT GGAATGCTCA ACAGCATCAA CACTGACATT 900

GACAACTTGT ATAGTCAAGG ACAAGAAGCA ATCAAAGTCT TTCAGAAGCT ACAAGGGATA 960

TGGGCCACTA TTGGAGCTCA GATAGAGAAT CTTCGCACCA CGTCCCTTCA AGAAGTCCAA 1020

GACTCTGATG ATGCTGATGA GATACAGATT GAACTTGAGG ACGCATCTGA TGCATGGTTA 1080

GTTGTGGCTC AAGAAGCTCG TGACTTCACA CTGAATGCCT ACTCAACCAA CAGTCGACAG 1140

AATCTCCCGA TCAATGTGAT CTCAGATTCA TGCAATTGCT CCACCACCAA CATGACATCC 1200

AATCAGTACA GCAATCCAAC AACCAACATG ACTAGCAATC AGTACATGAT TAGCCATGAG 1260

TATACCAGCT TGCCCAACAA CTTCATGTTG TCAAGGTAG 1299

(2) INFORMATION FOR SEQ ID NO:6:

(i) SEQUENCE CHARACTERISTICS:
(A) LENGTH: 432 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:6:

Met Gly Leu Ile His Thr Ile Lys Leu Asn Ser Asn Lys Lys Tyr Gly
1 5 10 15

Pro Gly Asp Met Thr Asn Gly Asn Gln Phe Ile Ile Ser Lys Gln Glu
20 25 30

Trp Ala Thr Ile Gly Ala Tyr Ile Gln Thr Gly Leu Gly Leu Pro Val
35 40 45

Asn Glu Gln Gln Leu Arg Thr His Val Asn Leu Ser Gln Asp Ile Ser
50 55 60

Ile Pro Ser Asp Phe Ser Gln Leu Tyr Asp Val Tyr Cys Ser Asp Lys
65 70 75 80

Thr Ser Ala Glu Trp Trp Asn Lys Asn Leu Tyr Pro Leu Ile Ile Lys
85 90 95

Ser Ala Asn Asp Ile Ala Ser Tyr Gly Phe Lys Val Ala Gly Asp Pro
100 105 110

Ser Ile Lys Lys Asp Gly Tyr Phe Lys Lys Leu Gln Asp Glu Leu Asp
115 120 125

Asn Ile Val Asp Asn Asn Ser Asp Asp Asp Ala Ile Ala Lys Ala Ile
130 135 140

Lys Asp Phe Lys Ala Arg Cys Gly Ile Leu Ile Lys Glu Ala Lys Gln
145 150 155 160

Tyr Glu Glu Ala Ala Lys Asn Ile Val Thr Ser Leu Asp Gln Phe Leu
165 170 175

His Gly Asp Gln Lys Lys Leu Glu Gly Val Ile Asn Ile Gln Lys Arg
180 185 190

Leu Lys Glu Val Gln Thr Ala Leu Asn Gln Ala His Gly Glu Ser Ser
195 200 205

Pro Ala His Lys Glu Leu Leu Glu Lys Val Lys Asn Leu Lys Thr Thr
210 215 220

Leu Glu Arg Thr Ile Lys Ala Glu Gln Asp Leu Glu Lys Lys Val Glu

```
225                          230                          235                          240

Tyr Ser Phe Leu Leu Gly Pro Leu Leu Gly Phe Val Val Tyr Glu Ile
                245                     250                     255

Leu Glu Asn Thr Ala Val Gln His Ile Lys Asn Gln Ile Asp Glu Ile
            260                     265                     270

Lys Lys Gln Leu Asp Ser Ala Gln His Asp Leu Asp Arg Asp Val Lys
        275                     280                     285

Ile Ile Gly Met Leu Asn Ser Ile Asn Thr Asp Ile Asp Asn Leu Tyr
    290                     295                     300

Ser Gln Gly Gln Glu Ala Ile Lys Val Phe Gln Lys Leu Gln Gly Ile
305                     310                     315                     320

Trp Ala Thr Ile Gly Ala Gln Ile Glu Asn Leu Arg Thr Thr Ser Leu
                325                     330                     335

Gln Glu Val Gln Asp Ser Asp Asp Ala Asp Glu Ile Gln Ile Glu Leu
            340                     345                     350

Glu Asp Ala Ser Asp Ala Trp Leu Val Val Ala Gln Glu Ala Arg Asp
        355                     360                     365

Phe Thr Leu Asn Ala Tyr Ser Thr Asn Ser Arg Gln Asn Leu Pro Ile
    370                     375                     380

Asn Val Ile Ser Asp Ser Cys Asn Cys Ser Thr Thr Asn Met Thr Ser
385                     390                     395                     400

Asn Gln Tyr Ser Asn Pro Thr Thr Asn Met Thr Ser Asn Gln Tyr Met
                405                     410                     415

Ile Ser His Glu Tyr Thr Ser Leu Pro Asn Asn Phe Met Leu Ser Arg
            420                     425                     430
```

( 2 ) INFORMATION FOR SEQ ID NO:7:

( i ) SEQUENCE CHARACTERISTICS:
( A ) LENGTH: 1140 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:7:

```
ATGGGTCTGA TTCACACAAT CAAGCTGAAC TCTAACAAGA AGTATGGTCC TGGCGATATG     60
ACTAACGGGA ACCAGTTCAT CATATCCAAG CAAGAATGGG CCACGATTGG CGCATACATT    120
CAGACTGGAC TCGGCTTACC AGTGAATGAG CAACAGCTGA GAACCCACGT TAACCTTAGT    180
CAAGACATCA GCATACCATC TGACTTTTCT CAACTCTACG ATGTGTATTG TTCTGACAAG    240
ACTAGTGCAG AATGGTGGAA CAAGAATCTC TATCCTTTGA TCATCAAGTC TGCCAATGAC    300
ATTGCTTCAT ATGGTTTCAA AGTTGCTGGT GATCCTTCGA TCAAGAAAGA TGGTTACTTC    360
AAGAAGCTTC AAGATGAACT CGACAACATT GTTGACAACA ACTCCGACGA CGATGCGATA    420
GCCAAAGCCA TCAAGGACTT CAAAGCAAGA TGTGGCATTC TCATCAAGGA AGCCAAGCAG    480
TATGAAGAAG CTGCCAAGAA CATTGTAACA TCATTGGATC AGTTTCTCCA TGGAGACCAG    540
AAGAAGCTCG AGGGTGTCAT CAACATTCAG AAACGTCTGA AAGAGGTTCA AACAGCTCTG    600
AATCAAGCCC ATGGGGAATC CAGTCCAGCT CACAAAGAGC TTCTTGAGAA AGTGAAGAAC    660
TTGAAGACCA CACTTGAGAG GACCATCAAA GCTGAACAAG ACTTGGAGAA GAAAGTAGAG    720
TACAGCTTTC TACTTGGACC CTTGTTAGGC TTTGTTGTCT ACGAGATTCT TGAGAACACT    780
GCTGTTCAAC ACATCAAGAA TCAAATCGAT GAGATCAAGA AACAGTTGGA TTCTGCGCAA    840
CATGACTTGG ATCGCGATGT GAAGATCATT GGAATGCTCA ACAGCATCAA CACTGACATT    900
```

-continued

```
GACAACTTGT ATAGTCAAGG ACAAGAAGCA ATCAAAGTCT TTCAGAAGCT ACAAGGGATA    960
TGGGCCACTA TTGGAGCTCA GATAGAGAAT CTTCGCACCA CGTCCCTTCA AGAAGTCCAA   1020
GACTCTGATG ATGCTGATGA GATACAGATT GAACTTGAGG ACGCATCTGA TGCATGGTTA   1080
GTTGTGGCTC AAGAAGCTCG TGACTTCACA CTGAATGCCT ACTCAACCAA CAGTCGATAG   1140
```

( 2 ) INFORMATION FOR SEQ ID NO:8:

( i ) SEQUENCE CHARACTERISTICS:
( A ) LENGTH: 380 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:8:

```
Met Gly Leu Ile His Thr Ile Lys Leu Asn Ser Asn Lys Lys Tyr Gly
1               5                   10                  15

Pro Gly Asp Met Thr Asn Gly Asn Gln Phe Ile Ile Ser Lys Gln Glu
            20                  25                  30

Trp Ala Thr Ile Gly Ala Tyr Ile Gln Thr Gly Leu Gly Leu Pro Val
        35                  40                  45

Asn Glu Gln Gln Leu Arg Thr His Val Asn Leu Ser Gln Asp Ile Ser
    50                  55                  60

Ile Pro Ser Asp Phe Ser Gln Leu Tyr Asp Val Tyr Cys Ser Asp Lys
65                  70                  75                  80

Thr Ser Ala Glu Trp Trp Asn Lys Asn Leu Tyr Pro Leu Ile Ile Lys
                85                  90                  95

Ser Ala Asn Asp Ile Ala Ser Tyr Gly Phe Lys Val Ala Gly Asp Pro
            100                 105                 110

Ser Ile Lys Lys Asp Gly Tyr Phe Lys Lys Leu Gln Asp Glu Leu Asp
        115                 120                 125

Asn Ile Val Asp Asn Asn Ser Asp Asp Asp Ala Ile Ala Lys Ala Ile
    130                 135                 140

Lys Asp Phe Lys Ala Arg Cys Gly Ile Leu Ile Lys Glu Ala Lys Gln
145                 150                 155                 160

Tyr Glu Glu Ala Ala Lys Asn Ile Val Thr Ser Leu Asp Gln Phe Leu
                165                 170                 175

His Gly Asp Gln Lys Lys Leu Glu Gly Val Ile Asn Ile Gln Lys Arg
            180                 185                 190

Leu Lys Glu Val Gln Thr Ala Leu Asn Gln Ala His Gly Glu Ser Ser
        195                 200                 205

Pro Ala His Lys Glu Leu Leu Glu Lys Val Lys Asn Leu Lys Thr Thr
    210                 215                 220

Leu Glu Arg Thr Ile Lys Ala Glu Gln Asp Leu Glu Lys Lys Val Glu
225                 230                 235                 240

Tyr Ser Phe Leu Leu Gly Pro Leu Leu Gly Phe Val Val Tyr Glu Ile
                245                 250                 255

Leu Glu Asn Thr Ala Val Gln His Ile Lys Asn Gln Ile Asp Glu Ile
            260                 265                 270

Lys Lys Gln Leu Asp Ser Ala Gln His Asp Leu Asp Arg Asp Val Lys
        275                 280                 285

Ile Ile Gly Met Leu Asn Ser Ile Asn Thr Asp Ile Asp Asn Leu Tyr
    290                 295                 300

Ser Gln Gly Gln Glu Ala Ile Lys Val Phe Gln Lys Leu Gln Gly Ile
```

-continued 305 310 315 320

Trp Ala Thr Ile Gly Ala Gln Ile Glu Asn Leu Arg Thr Thr Ser Leu
325 330 335

Gln Glu Val Gln Asp Ser Asp Asp Ala Asp Glu Ile Gln Ile Glu Leu
340 345 350

Glu Asp Ala Ser Asp Ala Trp Leu Val Val Ala Gln Glu Ala Arg Asp
355 360 365

Phe Thr Leu Asn Ala Tyr Ser Thr Asn Ser Arg Met
370 375 380

( 2 ) INFORMATION FOR SEQ ID NO:9:

( i ) SEQUENCE CHARACTERISTICS:
( A ) LENGTH: 1185 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: BACILLUS THURINGIENSIS
( C ) INDIVIDUAL ISOLATE: PS69D1

( v i i ) IMMEDIATE SOURCE:
( B ) CLONE: E. coli NM522(pMYC2317) NRRL B-18816

( i x ) FEATURE:
( A ) NAME/KEY: mat_peptide
( B ) LOCATION: 1..1185

( x i ) SEQUENCE DESCRIPTION: SEQ ID NO:9:

ATGATTTTAG GGAATGGAAA GACTTTACCA AAGCATATAA GATTAGCTCA TATTTTTGCA 60

ACACAGAATT CTTCAGCTAA GAAAGACAAT CCTCTTGGAC CAGAGGGGAT GGTTACTAAA 120

GACGGTTTTA TAATCTCTAA GGAAGAATGG GCATTTGTGC AGGCCTATGT GACTACAGGC 180

ACTGGTTTAC CTATCAATGA CGATGAGATG CGTAGACATG TTGGGTTACC ATCACGCATT 240

CAAATTCCTG ATGATTTTAA TCAATTATAT AAGGTTTATA ATGAAGATAA ACATTTATGC 300

AGTTGGTGGA ATGGTTTCTT GTTTCCATTA GTTCTTAAAA CAGCTAATGA TATTTCCGCT 360

TACGGATTTA AATGTGCTGG AAAGGGTGCC ACTAAAGGAT ATTATGAGGT CATGCAAGAC 420

GATGTAGAAA ATATTTCAGA TAATGGTTAT GATAAAGTTG CACAAGAAAA AGCACATAAG 480

GATCTGCAGG CGCGTTGTAA AATCCTTATT AAGGAGGCTG ATCAATATAA AGCTGCAGCG 540

GATGATGTTT CAAAACATTT AAACACATTT CTTAAAGGCG GTCAAGATTC AGATGGCAAT 600

GATGTTATTG GCGTAGAGGC TGTTCAAGTA CAACTAGCAC AAGTAAAAGA TAATCTTGAT 660

GGCCTATATG GCGACAAAAG CCCAAGACAT GAAGAGTTAC TAAAGAAAGT AGACGACCTG 720

AAAAAAGAGT TGGAAGCTGC TATTAAAGCA GAGAATGAAT TAGAAAAGAA AGTGAAAATG 780

AGTTTTGCTT TAGGACCATT ACTTGGATTT GTTGTATATG AAATCTTAGA GCTAACTGCG 840

GTCAAAAGTA TACACAAGAA AGTTGAGGCA CTACAAGCCG AGCTTGACAC TGCTAATGAT 900

GAACTCGACA GAGATGTAAA AATCTTAGGA ATGATGAATA GCATTGACAC TGATATTGAC 960

AACATGTTAG AGCAAGGTGA GCAAGCTCTT GTTGTATTTA GAAAAATTGC AGGCATTTGG 1020

AGTGTTATAA GTCTTAATAT CGGCAATCTT CGAGAAACAT CTTTAAAAGA GATAGAAGAA 1080

GAAAATGATG ACGATGCACT GTATATTGAG CTTGGTGATG CCGCTGGTCA ATGGAAAGAG 1140

-continued

ATAGCCGAGG AGGCACAATC CTTTGTACTA AATGCTTATA CTCCT 1185

( 2 ) INFORMATION FOR SEQ ID NO:10:

( i ) SEQUENCE CHARACTERISTICS:
( A ) LENGTH: 395 amino acids
( B ) TYPE: amino acid
( C ) STRANDEDNESS: single
( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
( A ) ORGANISM: BACILLUS THURINGIENSIS
( C ) INDIVIDUAL ISOLATE: PS69D1

( v i i ) IMMEDIATE SOURCE:
( B ) CLONE: E. coli NM522(pMYC2317) NRRL B-18816

( i x ) FEATURE:
( A ) NAME/KEY: Protein
( B ) LOCATION: 1..395

( x i ) SEQUENCE DESCRIPTION: SEQ ID NO:10:

| | | | | | | | | | | | | | | | |
|---|---|---|---|---|---|---|---|---|---|---|---|---|---|---|---|
| Met | Ile | Leu | Gly | Asn | Gly | Lys | Thr | Leu | Pro | Lys | His | Ile | Arg | Leu | Ala |
| 1 | | | | 5 | | | | | 10 | | | | | 15 | |
| His | Ile | Phe | Ala | Thr | Gln | Asn | Ser | Ser | Ala | Lys | Lys | Asp | Asn | Pro | Leu |
| | | | 20 | | | | | 25 | | | | | 30 | | |
| Gly | Pro | Glu | Gly | Met | Val | Thr | Lys | Asp | Gly | Phe | Ile | Ile | Ser | Lys | Glu |
| | | 35 | | | | | 40 | | | | | 45 | | | |
| Glu | Trp | Ala | Phe | Val | Gln | Ala | Tyr | Val | Thr | Thr | Gly | Thr | Gly | Leu | Pro |
| | 50 | | | | | 55 | | | | | 60 | | | | |
| Ile | Asn | Asp | Asp | Glu | Met | Arg | Arg | His | Val | Gly | Leu | Pro | Ser | Arg | Ile |
| 65 | | | | | 70 | | | | | 75 | | | | | 80 |
| Gln | Ile | Pro | Asp | Asp | Phe | Asn | Gln | Leu | Tyr | Lys | Val | Tyr | Asn | Glu | Asp |
| | | | | 85 | | | | | 90 | | | | | 95 | |
| Lys | His | Leu | Cys | Ser | Trp | Trp | Asn | Gly | Phe | Leu | Phe | Pro | Leu | Val | Leu |
| | | | 100 | | | | | 105 | | | | | 110 | | |
| Lys | Thr | Ala | Asn | Asp | Ile | Ser | Ala | Tyr | Gly | Phe | Lys | Cys | Ala | Gly | Lys |
| | | 115 | | | | | 120 | | | | | 125 | | | |
| Gly | Ala | Thr | Lys | Gly | Tyr | Tyr | Glu | Val | Met | Gln | Asp | Asp | Val | Glu | Asn |
| | 130 | | | | | 135 | | | | | 140 | | | | |
| Ile | Ser | Asp | Asn | Gly | Tyr | Asp | Lys | Val | Ala | Gln | Glu | Lys | Ala | His | Lys |
| 145 | | | | | 150 | | | | | 155 | | | | | 160 |
| Asp | Leu | Gln | Ala | Arg | Cys | Lys | Ile | Leu | Ile | Lys | Glu | Ala | Asp | Gln | Tyr |
| | | | | 165 | | | | | 170 | | | | | 175 | |
| Lys | Ala | Ala | Ala | Asp | Asp | Val | Ser | Lys | His | Leu | Asn | Thr | Phe | Leu | Lys |
| | | | 180 | | | | | 185 | | | | | 190 | | |
| Gly | Gly | Gln | Asp | Ser | Asp | Gly | Asn | Asp | Val | Ile | Gly | Val | Glu | Ala | Val |
| | | 195 | | | | | 200 | | | | | 205 | | | |
| Gln | Val | Gln | Leu | Ala | Gln | Val | Lys | Asp | Asn | Leu | Asp | Gly | Leu | Tyr | Gly |
| | 210 | | | | | 215 | | | | | 220 | | | | |
| Asp | Lys | Ser | Pro | Arg | His | Glu | Glu | Leu | Leu | Lys | Lys | Val | Asp | Asp | Leu |
| 225 | | | | | 230 | | | | | 235 | | | | | 240 |
| Lys | Lys | Glu | Leu | Glu | Ala | Ala | Ile | Lys | Ala | Glu | Asn | Glu | Leu | Glu | Lys |
| | | | | 245 | | | | | 250 | | | | | 255 | |
| Lys | Val | Lys | Met | Ser | Phe | Ala | Leu | Gly | Pro | Leu | Leu | Gly | Phe | Val | Val |
| | | | 260 | | | | | 265 | | | | | 270 | | |

-continued

| | | | | | | | | | | | | | | | |
|---|---|---|---|---|---|---|---|---|---|---|---|---|---|---|---|
| Tyr | Glu | Ile | Leu | Glu | Leu | Thr | Ala | Val | Lys | Ser | Ile | His | Lys | Lys | Val |
| | | 275 | | | | | 280 | | | | | 285 | | | |
| Glu | Ala | Leu | Gln | Ala | Glu | Leu | Asp | Thr | Ala | Asn | Asp | Glu | Leu | Asp | Arg |
| | 290 | | | | | 295 | | | | | 300 | | | | |
| Asp | Val | Lys | Ile | Leu | Gly | Met | Met | Asn | Ser | Ile | Asp | Thr | Asp | Ile | Asp |
| 305 | | | | | 310 | | | | | 315 | | | | | 320 |
| Asn | Met | Leu | Glu | Gln | Gly | Glu | Gln | Ala | Leu | Val | Val | Phe | Arg | Lys | Ile |
| | | | | 325 | | | | | 330 | | | | | 335 | |
| Ala | Gly | Ile | Trp | Ser | Val | Ile | Ser | Leu | Asn | Ile | Gly | Asn | Leu | Arg | Glu |
| | | | 340 | | | | | 345 | | | | | 350 | | |
| Thr | Ser | Leu | Lys | Glu | Ile | Glu | Glu | Glu | Asn | Asp | Asp | Asp | Ala | Leu | Tyr |
| | | 355 | | | | | 360 | | | | | 365 | | | |
| Ile | Glu | Leu | Gly | Asp | Ala | Ala | Gly | Gln | Trp | Lys | Glu | Ile | Ala | Glu | Glu |
| | 370 | | | | | 375 | | | | | 380 | | | | |
| Ala | Gln | Ser | Phe | Val | Leu | Asn | Ala | Tyr | Thr | Pro | | | | | |
| 385 | | | | | 390 | | | | | 395 | | | | | |